United States Patent [19]

Meyers et al.

[11] Patent Number: 5,932,561
[45] Date of Patent: Aug. 3, 1999

[54] DIETARY COMPOSITION WITH LIPID BINDING PROPERTIES FOR WEIGHT MANAGEMENT AND SERUM LIPID REDUCTION

[75] Inventors: Andrew E. Meyers, Boise; Mark R. Priddy, Meridian, both of Id.

[73] Assignee: Rexall Sundown, Inc., Boca Raton, Fla.

[21] Appl. No.: 08/957,447

[22] Filed: Oct. 24, 1997

[51] Int. Cl.⁶ .................................................... A61K 31/73
[52] U.S. Cl. .......................................... 514/55; 424/195.1
[58] Field of Search ............................ 514/55; 424/195.1

[56] References Cited

U.S. PATENT DOCUMENTS

| | | | |
|---|---|---|---|
| 4,223,023 | 9/1980 | Furda | 424/180 |
| 4,363,801 | 12/1982 | Nagyvary | 424/180 |
| 4,999,341 | 3/1991 | Ferro | 514/33 |
| 5,370,890 | 12/1994 | Sundfeld et al. | 426/417 |

FOREIGN PATENT DOCUMENTS 1277864  12/1990  Canada .

Primary Examiner—Kathleen K. Fonda
Attorney, Agent, or Firm—Pillsbury Madison & Sutro LLP

[57] ABSTRACT

A dietary supplement is provided that binds lipid to aid in weight loss and reduce cholesterol. The supplement includes chitosan, or a nutritionally acceptable derivative thereof, and aloin (especially aloe saponins); it can include at least one additional ingredient including any of betaine hydrochloride (betaine HCl), oat fiber or beta-glucan.

20 Claims, No Drawings

DIETARY COMPOSITION WITH LIPID BINDING PROPERTIES FOR WEIGHT MANAGEMENT AND SERUM LIPID REDUCTION

BACKGROUND OF THE INVENTION

1. Technical Field

The present invention relates generally to a dietary supplement composition which has lipid binding properties and, more particularly, to a composition that includes aloin (especially aloe saponins) and an amino polysaccharide such as, for example, chitosan.

2. Background

It is known that obesity and hyperphagia, or excessive eating, are both problems with behavioral and physiological components. It is also known that one drawback of some diets is that they do not work effectively on people with excessive appetites. The constant feeling of hunger in such people disturbs their daily activities. People suffering from appetite disorders are also often subjected to pyrosis or gastric burning (heartburn) and a sensation of acidity in their stomachs when not eating.

Chitin is an amino polysaccharide (poly-N-acetyl glucosamine) found in the exoskeleton of arthropods (e.g., crustaceans such as shrimp, crab and lobster; insects; and molluscs). The exoskeleton is the hard outer covering that functions as the mechanical supporting tissue of the body structure of such animals. Chitin is also found in some plants and fungi.

Chitosan is a natural product that can be derived from chitin, and is typically prepared by direct deacetylation of chitin in a caustic solution. Chitosan is a biopolymer similar in structure and properties to dietary fiber (e.g., vegetable bran, cellulose) but with additional dietary or nutritional advantages which are derived from its polycationic, or positively charged, structure. From a chemical standpoint, chitosan consists of polymerized D,L-glucosamine which is insoluble in water and in most common organic solvents. Unlike plant fiber like bran and cellulose, chitosan has the ability to absorb fat and other lipids in the intestine.

Chitosan also exists as a salt, and a number of chitosan salts are known and described in the literature. For example, N,O-carboxymethyl chitosan (NOCC) is obtained by reacting chitosan with monochloroacetic acid under alkaline conditions. The salts of chitosan generally show good solubility in water (e.g., acetate, citrate, formate and tartarate salts as described in U.S. Pat. No. 4,363,801).

Chitosan-lipid complexes are formed through bonds which can be attributed to the density of positive charges on chitosan. Due to chitosan's indigestibility, lipid absorption by the intestine is reduced. These characteristics make chitosan helpful in the treatment of high blood fat, hyperlipemia and high blood cholesterol, hypercholesteremia or hypertriglyceridemia. Through such complexes, chitosan is able to reduce the amount of lipid and cholesterol available for absorption and assimilation by the body.

One disadvantage of using chitosan for the aforementioned purpose is that it induces constipation, an undesirable condition that includes difficult and often painful elimination. Hence, the use of chitosan as a dietary supplement must be of a short duration or other ingredients or supplements added to combat the undesirable effects of the chitosan. U.S. Pat. No. 4,999,341 discloses the use of chitosan with soy saponins. The patent discloses combining soy saponins with chitosan so that the diarrhea-inducing soy saponins offset the constipating effect of chitosan. Other plant sources of saponins are listed in Table 1 of U.S. Pat. No. 5,370,890.

The present invention is directed to a dietary supplement that includes chitosan, or a functionally acceptable equivalent thereof, and aloin. Aloin contains aloe saponins which act as a laxative to offset the constipating effect of chitosan. However, aloe saponins have benefits not available from soy saponins in formulating the dietary supplement which include activities in the upper and lower gastrointestinal tract. In the upper gastrointestinal tract, aloe saponins act to increase desirable properties of chitosan: surface activating properties are increased to improve dispersion of chitosan and its capacity to bind fat, gel density is increased, and gel viscosity is increased. Furthermore, in the lower gastrointestinal tract, a laxative activity of the composition is produced locally by hydrolysis of barbaloin, a component of the aloe saponins, to aloe emodin which acts as a laxative by increasing water retention and mucus secretion in the large intestine. These and other beneficial properties of the present invention are further described below.

SUMMARY OF THE INVENTION

It is an object of the invention to provide a dietary composition with lipid binding properties.

An embodiment of the invention is a dietary composition comprised of the amino polysaccharide chitosan, or a functional equivalent thereof, and aloin. Aloin may be derived from aloe species such as, for example, *Aloe barbadensis* and *Aloe vulgaris*. Preferably, aloe saponins are included in the composition. The composition can also include one or more of betaine hydrochloride (betaine HCl), oat fiber or beta-glucan. The betaine hydrochloride enhances lipotropic activity and increases gastric acidity to improve the dispersion of chitosan in the stomach. The addition of oat fiber or beta-glucan improves the effectiveness of the composition by increasing bile acid secretion which helps to reduce total serum lipids.

The dietary compositions of the present invention may be used, for example, to aid in weight loss and weight management; to remove dietary fats, cholesterol, and other lipids from the digestive system and thereby reduce serum amounts of those lipids; and support digestive system function. In this aspect of the invention, the method of use comprises orally administering an effective amount of the chitosan composition to a subject (e.g., a human or other mammal) to achieve at least one of the aforementioned beneficial effects. Preferred subjects are those who would benefit from these effects such as, for example, an obese subject (e.g., greater than 10% above ideal body weight or as defined clinically) or a subject with high serum cholesterol levels (e.g., greater than 200 milligrams/deciliter serum cholesterol).

DETAILED DESCRIPTION OF THE INVENTION

The composition formed by combining the amino polysaccharide chitosan, or a functional equivalent thereof, with aloin (preferably including aloe saponins), and optionally one or more of betaine hydrochloride (HCl), oat fiber or beta-glucan, has unexpected properties that are useful for a dietary supplement. The chitosan may be deacetylated between about 75 to about 95%, preferably about 80% deacetylated. In any embodiment of the invention, the preferred ratio of the amino polysaccharide, preferably chitosan, is about 2000 to about 3000 parts by weight, and the preferred ratio of the aloe saponins is about 1 to about 10 parts by weight. The amount of chitosan included can range from about 100 to about 10,000 parts by weight, preferably from about 500 to about 6000 parts by weight, and more preferably from about 2000 to about 3000 parts by weight. The range for aloe saponins in any embodiment can range from about 1 to about 1000 parts by weight, preferably from about 1 to about 100 parts by weight, and more preferably from about 1 to about 10 parts by weight.

In other embodiments one or more of the components of betaine hydrochloride (betaine HCI), oat fiber or beta-glucan can be added to the amino polysaccharide and aloin. For example, an embodiment of the invention can be formulated which includes chitosan, aloin, and betaine HCI. The preferred ratio of the betaine HCI in any embodiment is about 200 parts by weight. The amount of betaine HCI included in any embodiment of the invention can range from about 50 to about 1000 parts by weight. Another embodiment with betaine HCI can be formulated that includes chitosan, aloin, betaine HCI, and oat fiber. A further betaine HCI embodiment can be formulated to include chitosan, aloin, betaine HCI and beta-glucan. Another betaine HCI formulation can include chitosan, aloin, betaine HCI, oat fiber and beta-glucan.

In any embodiment that includes oat fiber in the formulation, the preferred ratio is about 2,000 to about 4,000 parts by weight. The amount of oat fiber included in any embodiment can range from about 50 to about 15,000 parts by weight. One embodiment of the invention that can be formulated with oat fiber would include chitosan, aloin, and oat fiber. An oat fiber embodiment that also includes beta-glucan is chitosan, aloin, oat fiber and beta-glucan. Other embodiments formulated with oat fiber have been described above, in conjunction with the betaine HCI embodiments.

Turning to embodiments that include beta-glucan, the preferred ratio is about 2,000 to about 4,000 parts by weight. In addition to the embodiments formulated with beta-glucan described herein, an embodiment with beta-glucan could include chitosan, aloin, betaine HCI, and beta-glucan.

As set forth above, an embodiment with all of the described ingredients would include chitosan, aloin, betaine HCI, oat fiber and beta-glucan.

Average daily dosages for individuals using the present invention may range from about 500 milligrams per day to about 6000 milligrams per day of chitosan. Special conditions may warrant additional dosages. The dosage is somewhat independent of the subject's body weight and more directly related to the fat content of the diet the subject wishes to offset. The average amount of aloe saponins in this daily dosage may range from about 1 milligram to about 10 milligrams.

The following examples are meant to be illustrative of the present invention; however, the practice of the invention is not limited or restricted in any way by them.

Exemplary formulations of the invention are as follows:

| Formulation 1 | |
| --- | --- |
| chitosan | 3,000 mg |
| aloe saponin | 10 mg |
| Formulation 2 | |
| chitosan | 3,000 mg |
| aloe saponin | 10 mg |
| betaine HCl | 200 mg |
| Formulation 3 | |
| chitosan | 2,000 mg |
| aloe saponin | 10 mg |
| beta-glucan | 3000 mg |
| Formulation 4 | |
| chitosan | 3,000 mg |
| aloe saponin | 10 mg |
| betaine HCl | 200 mg |
| oat fiber | 2,000 mg |

-continued

| Formulation 5 | |
| --- | --- |
| chitosan | 3,000 mg |
| aloe saponin | 10 mg |
| betaine HCl | 200 mg |
| oat fiber | 3,000 mg |
| beta-glucan | 3,000 mg |

In a 12-day double-blind, placebo controlled study, the fat-binding capacity of the present invention was shown in 55 human subjects. The dietary supplement contained 2000 mg of chitosan, 10 mg of aloe saponins, 200 mg of betaine HCI, and 175 mg of oat fiber in capsule form. The placebo was a calcium carbonate base. Analysis of fat-binding capacity was conducted fecal fat measurements collected from 24 hour stool samples. A baseline sample was taken at day 3 as a baseline and then supplementation with the present invention or placebo was initiated. Follow-up stool samples were collected on days 10, 11 and 12. The following illustrates the outcome of the study:

Fecal Fat Readings per 24 Hour Stool Sample

| Day | Placebo | Invention | % Difference |
| --- | --- | --- | --- |
| 3 | 2.59 | 2.80 | 8.1% |
| 10 | 2.71 | 3.30 | 21.7% |
| 11 | 1.90 | 2.45 | 28.9% |
| 12 | 1.85 | 3.03* | 63.8% |

*statistically significant ($p > 0.05$)

The mean fecal fat values indicated a progressive trend towards increasing fat binding capability in the subjects supplemented with the composition of the present invention. At day 12, the statistically significant difference between the placebo and the invention showed a 63.8% increased binding capacity for fats in subjects using the present invention. These results demonstrated that chitosan can bind fats in stoichiometric amounts (i.e., binding up to 4 to 5 times its weight in fats).

An advantage of the present invention is that desirable characteristics and activities of the components are maintained and enhanced, while the undesirable effects, such as dysfunctional bowels, are reduced.

Other advantages of the invention appear to be attributable to greater availability of chitosan. In the acidic environment of the stomach, chitosan acts as a soluble fiber, distributed among the digestive secretions and food particles. Binding several times its weight in water, chitosan begins to form a gel capable of absorbing dietary lipids in a pH-dependent manner. As it passes through the non-acidic conditions of the small and large intestines, chitosan becomes insoluble and forms a gel-like complex that bonds with lipids and bile acids. This insoluble complex passes undigested through the intestines and is naturally eliminated from the body.

Chitosan binding capacity can be measured in vitro by applying powdered chitosan fiber to a measured amount of fat (e.g., peanut oil). Chitosan fiber is added to the oil in incremental amounts until the oil is saturated or supersaturated. Mechanical mixing of the two components ensures a homogeneous mixture and fat absorption by the chitosan fiber. Once the oil is completely saturated, a ratio of relative amounts may be calculated. Other parameters such as, for example, the addition of other active ingredients of the present invention or pH may be assayed similarly.

Aloe saponins are able to increase surface activating properties of chitosan, increasing its dispersion and lipid binding capabilities. The aloe saponins also increases the gel density and gel viscosity of the chitosan. In particular, chitosan more readily forms gels with gastric liquids in the presence of the aloe saponins. In vitro, for example, the gelification rate of chitosan in gastric juice is about 3 to 5 times higher if aloe saponins are present. Moreover, the thus formed gel is more dense and more viscous, even with the concentration of chitosan being the same.

The aloe saponins contain aloe emodin, which is a breakdown product of barbaloin, which is produced by bacterial activity in the human intestine (Che et al., Planta Med., 57:15–19, 1991; Hattori et al., Pharmacology, 47:125–133, 1993), resulting in additional laxative activity for the present invention. The aloe saponins increase water retention and mucus secretion in the large intestine, both of which can advantageously treat difficult and painful elimination associated with constipation (Akao et al., Biol. Pharm. Bull., 19:136–138, 1996). The increased water retention in the lower intestine and increased mucus secretion aids in improving the function of the digestive system with respect to regularity and preventing constipation (Ishii et al., Chem. Pharm. Bull., 38:197–200, 1990; Ishii et al., Biol. Pharm. Bull., 17:651–653,1994).

It has been furthermore observed that the oily emulsions formed with saponins are more stable in the presence of chitosan, mainly because the emulsifying action of the aloe saponins is enhanced by the amino polysaccharides.

The betaine HCI functions as a gastric acidifier and has lipotropic activity which promotes the transportation and utilization of lipids, and prevents their accumulation in the liver. Betaine HCI under hydrolysis yields hydrochloric acid, which in turn increases gastric acidity. Increased gastric acidity increases chitosan dispersion in the stomach, yielding an increased surface area for binding and emulsifying lipids. As a lipotropic factor, betaine acts on the liver to improve lipid metabolism and excretion. The increased gastric activity creates a more effective environment for chitosan's action, in concert with the aloe saponins and betaine. Other acceptable salts of betaine (e.g., citric) would function as a gastric acidifier but would not have lipotropic activity.

Oat fiber and beta-glucan increase bile acid secretion and decrease serum lipids. Beta-glucan is a soluble fiber found within oat fiber. Beta-glucan has been shown to increase bile acid secretion leading to a reduction in total serum lipids including cholesterol and low density lipoproteins (LDL). There is increased liver activity and increased bile acid secretion.

The association of chitosan with aloe saponins is endowed with the following activities: antihyperlipemic, anticholesterolemic, lipoperoxidasic, hepatoprotective, limiting liquid absorption in the large and small intestines, appetite moderating, and antigastritic.

The last two activities (i.e., appetite moderating and antigastritic) characterize the association of chitosan and aloe saponin, and represent properties not inherent in either ingredient separately. Without any secondary effects, such as compaction or diarrhea, and without any sign of intolerability even in the case of extended treatments, the association between the amino polysaccharide chitosan and the aloe saponins can be used as for weight loss or weight management, even if the same amount of calories is ingested. Due to the capability of the composition to complex with and render indigestible part of the food lipids which are ingested, the calories ingested in alimentary form are made unavailable to the subject.

Such an association has all the advantages of dietetic vegetable fibers and can also, from a functional standpoint, be defined as an animal bran, with all of the advantages of a true or plant bran. Moreover the composition has the property of complexing with lipids, which is a property of amino polysaccharide structures which have been made surface active.

By having recourse to suitable dosages, a negative caloric balance can be obtained in the case of obesity and hyperphagia. Moreover, the appetite moderating effect of the invention helps alleviate the discomfort resulting from typical hunger sensations. The gastroprotective action of the invention furthermore helps prevent pyrosis and burning sensations, as well as the acid sensation often reported by patients suffering from digestive associated disorders, such as dysphagia and disorderly alimentation.

The present invention can be administered in pill or tablet form. Tablets can, if desired, be coated or uncoated. Suitable tableting procedures include those generally described in Perry's Chemical Engineer's Handbook, page 8–62 to 8–64 ($4^{th}$ Edition 1963), Ullmann's Encyclopedia of Industrial Chemistry, volume A19, pages 245–256 (Springer Verlag 1991), Ullmann's Encyclopedia of Industrial Chemistry, volume B2, pages 7–31 to 7–37 (Springer Verlag 1988), and Lieberman (editor), Pharmaceutical Dosage Forms: Tablets, volumes 1 and 2 (Marcel Dekker 1980). The composition can also be administered in capsule form. The size of each dosage and the interval of dosing to the patient effectively determines the size and shape of the tablet or capsule. By present preference, each tablet or capsule contains the active ingredients in predetermined amounts to simplify treatment of the subject.

The present therapeutic composition can be administered orally. Oral administration is preferred because of convenience to the subject as well as the dosing schedule.

The composition can also include other additives known in the nutritional and pharmaceutical arts such as, for instance, an acceptable carrier vehicle, diluent, binder, stabilizer, preservative, or combinations thereof as described in Remington's Pharmaceutical Science by E. W. Martin. The relative amounts of active ingredients within a dose, or a dosing schedule can be adjusted appropriately for efficacious administration to the subject.

The method of use comprises administering an effective amount of one of the dietary supplement compositions described above. As used herein, "effective amount" means an amount of the composition sufficient to produce at least one of the aforementioned desired effects with statistical significance. For example, the amount of dietary fat ingested by the human or other mammalian subject can determine the amount of composition to be administered to achieve a statistically significant removal of fat from the digestive system. Although the effective amount may vary with such factors as caloric intake, body weight and physical health, a preferred effective daily dose will include 2000 milligrams of chitosan, 10 milligrams of aloe saponins, 200 milligrams of betaine hydrochloride, and 175 milligrams of oat fiber.

All texts, articles and patents cited in this specification are incorporated herein by reference in their entirety.

The invention has been described with reference only to the active ingredients, to illustrate and further the understanding of the invention. The ratios given relate to the relationship between the aforementioned ingredients only. It is recognized that one skilled in the relevant art would understand that desired carriers and/or inert compounds can be added to any formulation, if the above described ratio relationships between the active constituents are respected. It is contemplated that other chemical compounds or functional groups may bond with the active ingredients such as, for example, salts of chitosan. Any such derivatives that are nutritionally acceptable may be used in embodiments of this invention that were herein described and still be within the contemplated scope of this invention. While there is shown and described a preferred embodiment of the invention, it is to be distinctly understood that this invention is not limited thereto but may be variously embodied to practice within the scope of the following claims.

We claim:

1. A dietary composition comprised of:
   (a) a chitosan amino polysaccharide, and
   (b) aloin.
2. The composition of claim 1, wherein the aloin includes barbaloin.
3. The composition of claim 1, wherein the amino polysaccharide is present in an amount from 100 to 10,000 parts by weight.
4. The composition of claim 1, wherein the aloin includes aloe saponins present in an amount from 1 to 1000 parts by weight.
5. The composition of claim 1, further comprising betaine hydrochloride.
6. The composition of claim 5, further comprising oat fiber.
7. The composition of claim 5, further comprising beta-glucan.
8. A method of using a dietary composition comprising orally administering the composition to a human or other mammal, wherein the composition comprises:
   (a) a chitosan amino polysaccharide, and
   (b) aloin.
9. The method of claim 8, wherein the aloin includes barbaloin.
10. The method of claim 9, wherein the barbaloin is hydrolyzed by the human or other mammal to aloe emodin.
11. The method of claim 8, wherein the amino polysaccharide in the composition is present in an amount from 100 to 10,000 parts by weight.
12. The method of claim 8, wherein the aloin in the composition includes aloe saponins present in an amount from 1 to 1000 parts by weight.
13. The method of claim 8, wherein the composition further comprises betaine hydrochloride.
14. The method of claim 13, wherein the composition further comprises oat fiber.
15. The method of claim 13, wherein the composition further comprises beta-glucan.
16. The method of claim 8, wherein the human or other mammal is obese.
17. The method of claim 8, wherein the human or other mammal has a serum cholesterol greater than 200 milligram/deciliter prior to administration of the composition.
18. The method of claim 13, wherein gastric acidity of the human or other mammal is increased after administration of the composition.
19. The method of claim 13, wherein bile acid secretion in the human or other mammal is increased after administration of the composition.
20. The method of claim 13, wherein intestinal water retention and mucus secretion in the human or other mammal is increased after administration of the composition.

* * * * *